(12) United States Patent
Huang et al.

(10) Patent No.: US 8,049,050 B2
(45) Date of Patent: Nov. 1, 2011

(54) METHOD FOR PRODUCING EXO-THDCPD AND ADAMANTANE USING PSEUDO-FIXED BED IONIC LIQUID REACTOR

(75) Inventors: Ming-Yu Huang, Chiayi (TW); Jen-Chun Chang, Chiayi (TW); Jann-Chen Lin, Chiayi (TW); Kun-Hai Lin, Chiayi (TW); Jung-Chung Wu, Chiayi (TW)

(73) Assignee: CPC Corporation, Taiwan, Taipei (TW)

( * ) Notice: Subject to any disclaimer, the term of this patent is extended or adjusted under 35 U.S.C. 154(b) by 360 days.

(21) Appl. No.: 12/463,732

(22) Filed: May 11, 2009

(65) Prior Publication Data

US 2010/0286460 A1  Nov. 11, 2010

(51) Int. Cl.
*C07C 5/25* (2006.01)

(52) U.S. Cl. ............ 585/363; 585/377; 585/669

(58) Field of Classification Search .......... None
See application file for complete search history.

(56) References Cited

U.S. PATENT DOCUMENTS

| 4,270,014 A | * | 5/1981 | Norton et al. ............ 585/22 |
| 7,488,860 B2 | * | 2/2009 | Huang et al. ............ 585/363 |
| 7,744,838 B2 | * | 6/2010 | Davis, Jr. .............. 423/220 |

* cited by examiner

*Primary Examiner* — Tam M Nguyen

(74) *Attorney, Agent, or Firm* — Morris Manning Martin LLP; Tim Tingkang Xia, Esq.

(57) ABSTRACT

A method for synthesizing exo-tetrahydrodicyclopentadiene (exo-THDCPD) and adamantane is provided, including isomerization of an endo-tetrahydrodicyclopentadiene (endo-THDCPD) as a reaction feed with an acidic ionic liquid of aluminum trichloride in a pseudo-fixed bed ionic liquid reactor. Reactants float as a droplet from bottom to top of the pseudo-fixed bed reactor, and finally are discharged from a side tube. A mole fraction of aluminum trichloride in the acidic ionic liquid of aluminum trichloride is from 0.5 to 0.9, a feeding rate of the reaction feed is 0.1-10 g/min, and a temperature for the isomerization is between 25-120° C.

10 Claims, 2 Drawing Sheets

METHOD FOR PRODUCING EXO-THDCPD AND ADAMANTANE USING PSEUDO-FIXED BED IONIC LIQUID REACTOR

BACKGROUND OF THE INVENTION

1. Field of the Invention

The present invention relates to an isomerization process of tricycloalkane, applicable in a catalytic reaction with an ionic liquid having high activity and immiscible with reactants, and particularly applicable in isomerization of tricycloalkane such as endo-tetrahydrodicyclopentadiene (endo-THDCPD) and exo-tetrahydrodicyclopentadiene (exo-THDCPD) with an acidic ionic liquid of aluminum trichloride.

2. Related Art

Since many years ago, acidic catalysts have been applied in oil refining and petrochemical industries, including processes such as cracking, alkylation, isomerization, polymerization, etherification, esterification, acylation and transesterification. Traditional Lewis acid such as aluminum trichloride ($AlCl_3$) and boron trifluoride ($BF_3$) and Bronsted acid such as hydrofluoric acid (HF) and sulfuric acid ($H_2SO_4$) are used as catalyst and have effective catalytic activity, in most of alkylation and isomerization. However, some persistent difficulties are still in existence, for example, problems existed in product separation, catalyst recovery, equipment corrosion, treatment of acidic waste water and massive spent catalyst. Therefore, both industrial and academic circles have actively endeavored to research them, with expectation to develop a solid strong acid or superacid catalyst to replace the traditional liquid acids in the processes.

One improved process is to directly load anhydrous aluminum trichloride ($AlCl_3$) onto a support of inorganic material, to prepare a loaded Lewis acid, which has good reaction activity and selectivity in, for example, catalytic cracking of hydrocarbons, isomerization of aromatic hydrocarbons, and alkylation, and also improve the disadvantages above. In addition, montmorrilonite, polymer, and molecular sieve are also used as support to prepare loaded aluminum trichloride ($AlCl_3$) catalysts, all of which can exhibit good activity and selectivity. Commercial applications thereof are supposed to be broadened if breakthroughs in selection of support, loading technology, and regeneration process can be achieved in future.

Solid acids have disadvantages while being convenient in application, for example, difficulty in contact with reactants. Furthermore, because aluminum trichloride ($AlCl_3$) reacts with hydroxyl (—OH) on a surface of its support and leads to a species containing —O—$AlCl_2$ group, acidity is lowered, and activity decline is easily caused by carbon accumulation because of high reaction temperature.

Therefore, use of an acidic ionic liquid is another preferred selection, in that its properties, such as acidity and solubility, can be optionally adjusted, and reactants and reaction products can be easily separated from the ionic liquid catalyst, i.e. they are in an immiscible liquid-liquid biphasic system.

The ionic liquid will gradually play an important role in catalytic process in future green chemistry industry, since it has no vapor pressure, can be adjusted for acidity and solubility by cation and anion species and their molar ratios to aluminum trichloride, and thus can perform a catalytic reaction effectively.

SUMMARY OF THE INVENTION

Accordingly, the present invention is directed to a method for synthesizing exo-tetrahydrodicyclopentadiene (exo-THDCPD), by isomerizing endo-tetrahydrodicyclopentadiene (endo-THDCPD) with a strong acidic ionic liquid in a pseudo-fixed bed reactor.

The present invention is further directed to a method for synthesizing adamantane, by isomerizing exo-THDCPD with a strong acidic ionic liquid in a pseudo-fixed bed reactor.

The present invention proposes a method for synthesizing exo-THDCPD using a pseudo-fixed bed ionic liquid reactor, by isomerizing an endo-THDCPD as a reaction feed with an acidic ionic liquid of aluminum trichloride in a pseudo-fixed bed reactor. Reactants float as a droplet from bottom to top of the pseudo-fixed bed reactor, and finally are discharged from a side tube, in which a mole fraction of aluminum trichloride in the acidic ionic liquid of aluminum trichloride is from 0.5 to 0.9, a feeding rate of the reaction feed is 0.1-10 g/min, and a temperature for the isomerization is between 25-120° C.

The present invention also proposes a method for synthesizing adamantane using a pseudo-fixed bed ionic liquid reactor, by isomerizing an exo-THDCPD as a reaction feed with an acidic ionic liquid of aluminum trichloride in a pseudo-fixed bed reactor. Reactants float as a droplet from bottom to top of the pseudo-fixed bed reactor, and finally are discharged from a side tube, in which a mole fraction of aluminum trichloride in the acidic ionic liquid of aluminum trichloride is from 0.5 to 0.9, a feeding rate of the reaction feed is 0.1-10 g/min, and a temperature for the isomerization is between 25-120° C.

In the present invention, isomerization of tricycloalkane such as endo-THDCPD and exo-THDCPD is achieved by mainly utilizing properties in which the ionic liquid is immiscible with reactants and reaction products, and they have very different specific gravity, and thus layer separation is easily to occur, and feasibility of this simple and effective process is illustrated by varying conditions such as reaction temperature, feeding rate, and packing in column.

In order to make content of the present invention more comprehensible, preferred embodiments of the present invention are described below with reference to the accompanying drawings.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below for illustration only, and thus are not limitative of the present invention, and wherein.

DETAILED DESCRIPTION OF THE INVENTION

Figure 1:
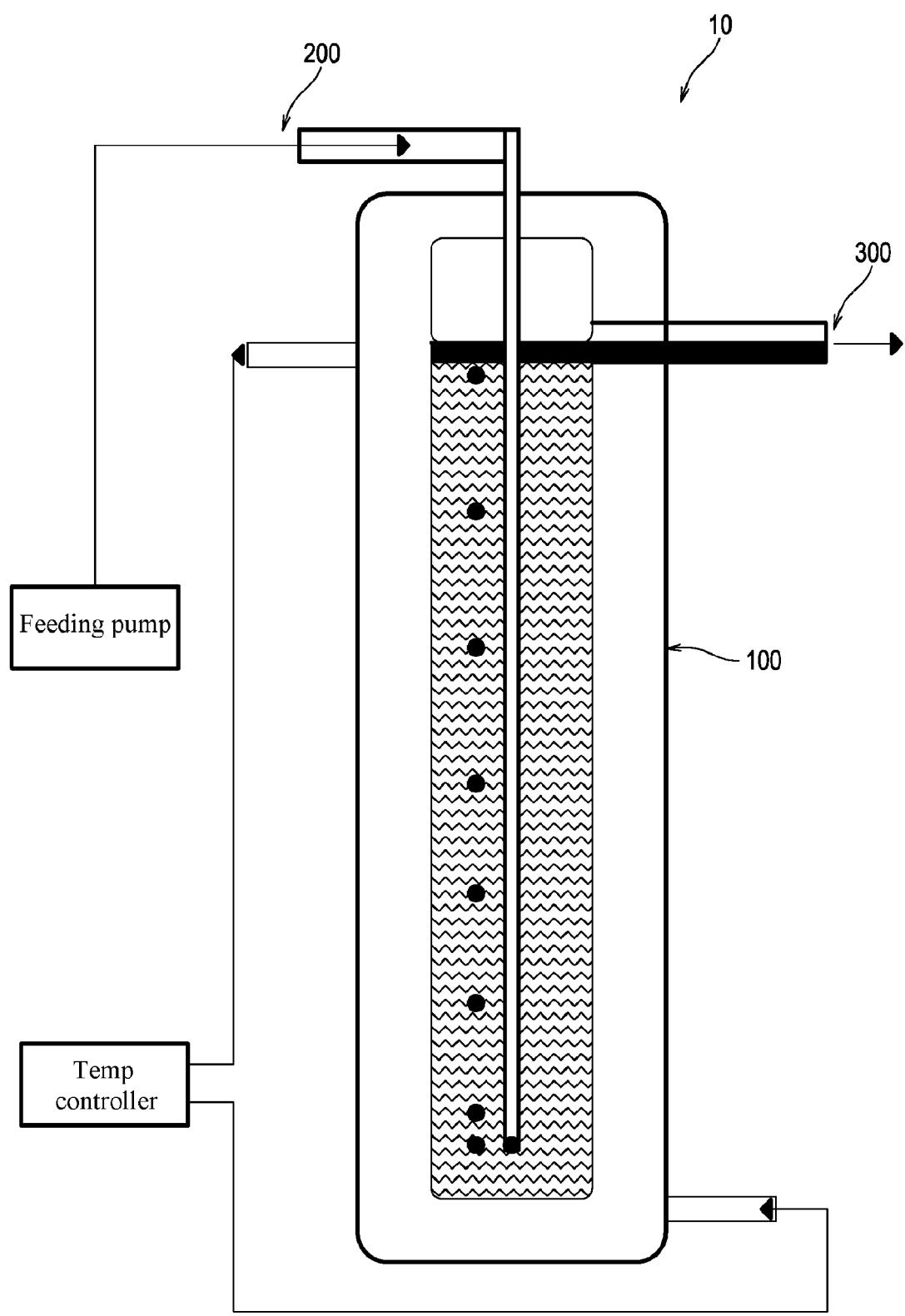
FIG. 1 schematically shows a pseudo-fixed bed reactor without glass bead.

In following description, same reference numerals and designations are used for elements having identical or similar functions and structures in different embodiments, for purpose of consistency in description of the present invention.

Figure 2:
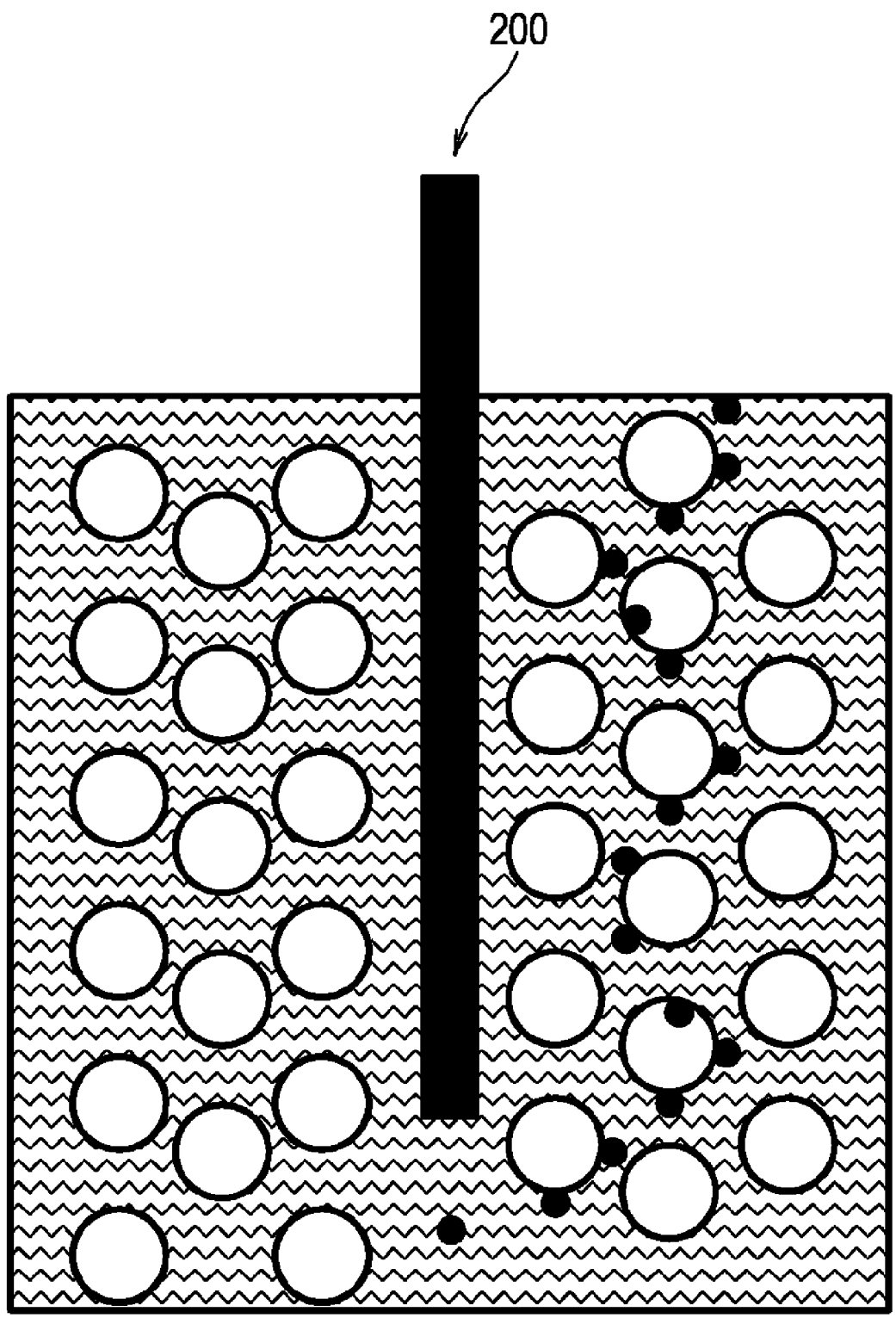
FIG. 2 schematically shows a bottom view of a pseudo-fixed bed reactor filled with glass bead.

FIG. 1 shows a schematic view of a pseudo-fixed bed reactor without glass bead; and FIG. 2 shows a schematic bottom view of a pseudo-fixed bed reactor filled with glass bead. Referring to FIGS. 1 and 2, the pseudo-fixed bed reactor 10 includes, in term of structure, a glass reaction column 100, a feeding end 200, a discharge end 300, a feeding pump, and a temp controller.

Embodiment I

Influence of Reaction Temperature 41.48 g of pyridine hydrochloride (PHC) and 88.89 g of aluminum trichloride ($AlCl_3$) were stirred and fully mixed in a glass round-bottom flask in a glove box, to give an ionic liquid, which was then poured into a glass reaction column (length: 45 cm, and inner diameter: 3.0 cm) and covered with a layer of cyclohexane, and then the glass reaction column was placed in a continuous reaction system (as shown in FIG. 1).

Reaction feeds endo-THDCPD/cyclohexane (w/w=1/1) were first placed in a glass feeding vessel filled with molecular sieve, in which positive pressure was formed with nitrogen. The glass reaction column was externally heated with thermostat circulating water, stabilized at 50° C., and then charged with the feeds by a LC pump (1.0 g/min). The reactants floated as a droplet from bottom to top of the ionic liquid. Samples were taken at a 10 min interval for analysis, then temperature of the circulating water was raised to 60° C. after conversion rate was stable, next, samples were taken again at a 10 min interval for analysis after the temperature is stable, and reactions at other temperatures were carried out following same steps as above. Experiment results show that the droplet floats from bottom to top of the ionic liquid, and has a contact time with the ionic liquid in the column of about 5-6 s. Conversion rates at different temperatures are provided in table 1. The results indicate that the conversion rate of endo-THDCPD is increased with the reaction temperature, and is up to 10.7% by reaction in the 45 cm column at 80° C.

TABLE 1

Reaction results of endo-THDCPD at different temperatures

| | Reaction Temperature, ° C. | | | |
|---|---|---|---|---|
| | 50 | 60 | 70 | 80 |
| Conversion Rate of endo-THDCPD, % | 1.8 | 2.2 | 4.5 | 10.7 |
| Selectivity of Exo-THDCPD, % | 100 | 100 | 100 | 100 |

Embodiment II

Influence of Feeding Rate

Similar to conditions described in Embodiment I, different feeding rates (0.5, 1.0, 1.5, and 2.0 g/min) were separately employed at 50° C. and 70° C., and samples were taken at a 10 min interval for analysis, until the conversion rate is stable. The experiment results are provided in table 2 and indicate that the droplet is increased in size as the feeding rate is increased, so floating-up rate is increased, and thus contact time with the ionic liquid is reduced, and contact area are also decreased, leading to decreased conversion rate. If the feeding rate can be enhanced in the same small droplet state, then space time yield can be effectively improved.

TABLE 2

Influence of feeding rate on conversion rate

| Reaction Temperature | 50° C. | Feeding Rate, g/min | 0.5 | 1.0 | 1.5 | 2.0 |
|---|---|---|---|---|---|---|
| | | Conversion Rate of Endo-THDCPD, % | 2.3 | 1.6 | 1.1 | 0.7 |
| | | Space Time Yield of Exo-THDCPD, g/hr | 0.34 | 0.48 | 0.50 | 0.42 |
| | 70° C. | Feeding Rate, g/min | 0.5 | 1.0 | 1.5 | 2.0 |
| | | Conversion Rate of Endo-THDCPD, % | 6.6 | 4.5 | 2.3 | 1.1 |
| | | Space Time Yield of Exo-THDCPD, g/hr | 1.98 | 2.70 | 2.07 | 1.32 |

Embodiment III

Cycle Reaction Test on Product

Feeds endo-THDCPD/cyclohexane 1/1 (w/w) (60 g) in the feeding vessel were fed at a rate of 1.0 g/min at 70° C. into the ionic liquid column from bottom, the feeding droplet spontaneously floated to top of the column, then discharged from a side tube to return back to the feeding vessel to be mixed. The cycle reaction was performed for 5 h in this way. Analysis of components in mixed product in the feeding vessel was performed every hour. Results are provided in table 3, and indicate that conversion rate of endo-THDCPD increases with the cycle time, which is equivalent to results obtained with an equivalent fold elongated column, i.e. residence time of the droplet in the ionic liquid column grows.

The results suggest that if length of the reaction column can be suitably extended, then reaction conversion rate is supposed to reach to 100% in a single pass through the ionic liquid column under same reaction conditions.

TABLE 3

Influence of cycle reaction of product on conversion rate and selectivity

| | Cycle Reaction Time, hr | | | | |
|---|---|---|---|---|---|
| | 1 | 2 | 3 | 4 | 5 |
| Conversion Rate, % | 4.5 | 7.8 | 10.6 | 13.5 | 17.1 |
| Selectivity % exo-THDCPD | 100 | 98.9 | 98.8 | 98.7 | 97.9 |
| Adamantane | 0 | 0 | 0 | 0 | 0.2 |
| Alkyl-THDCPD | 0 | 1.1 | 1.2 | 1.3 | 1.9 |
| di-THDCPD | 0 | 0 | 0 | 0 | 0 |

Embodiment IV

Influence of Small Glass Bead Filled in Reaction Column

Because the conversion rate increases with the residence time of the feed droplet in the ionic liquid column, packing such as small glass bead can be filled in the column, to extend pathway of the droplet in the column. The small glass bead had a diameter of 5 mm, and 45 ml glass bead was added into a column of 318 ml in total. With endo-THDCPD as feed, reaction results at 70° C. are shown in table 4, and indicate that filling packing such as glass bead can improve the reaction conversion rate.

TABLE 4

Activity comparison with and without small glass bead filled in reaction column

| | | Feeding Rate, g/min | | |
|---|---|---|---|---|
| | | 0.5 | 1.0 | 2.0 |
| Without Glass Bead | Conversion Rate of Endo-THDCPD, % | 6.6 | 4.5 | 1.1 |
| | Selectivity of Exo-THDCPD, % | 100 | 100 | 100 |
| With Glass Bead | Conversion Rate of endo-THDCPD, % | 10.3 | 6.5 | 2.7 |
| | Selectivity of Exo-THDCPD, % | 100 | 100 | 100 |

Embodiment V

Cycle Reaction Test on Product (Exo-THDCPD as Feed)

Reaction was carried out at 70° C. in an ionic liquid column filled with small glass bead, with 100% exo-THDCPD (JP-10) as feed, following the steps in Embodiment III (1.0 g/min). Results are provided in table 5 and indicate that the conversion rate of exo-THDCPD increases with cycle time.

TABLE 5

Influence of cycle reaction of product on synthesis of adamantane

| | | Cycle Reaction Time, hr | | | | |
|---|---|---|---|---|---|---|
| | | 1 | 2 | 3 | 4 | 5 |
| Conversion Rate, % | | 0.1 | 0.16 | 0.28 | 0.35 | 0.55 |
| Selectivity % | Adamantane | 100 | 100 | 100 | 100 | 100 |
| | Decalin | 0 | 0 | 0 | 0 | 0 |
| | Bicyclic | 0 | 0 | 0 | 0 | 0 |

Generally, for a biphasic catalytic reaction system, because reactants are immiscible with catalyst, stirring and mixing are necessary to increase contact between them, and improve catalytic activity. After reaction, by standing for separation, upper layer of reactants and products can be easily decanted and separated, and lower layer of ionic liquid catalyst will be recycled to reaction system for further reaction.

Where acidity of the ionic liquid is changed and reaction temperature is raised, quite high reaction rate can be achieved, at this time, reaction liquid can be as a droplet fed to bottom of the ionic liquid column by a pump, and just like air bubbles, gradually floats to top of the ionic liquid column by rising force in the ionic liquid, to form an immiscible product layer which is then spontaneously discharged from a side tube.

Therefore, elongating ionic liquid column, raising reaction temperature, and filling packing in the column all can effectively improve conversion rate for each pass through the column reactor.

In view of this, in the present invention, endo-THDCPD can be isomerized into exo-THDCPD (JP-10), or exo-THDCPD isomerized into adamantane, in a pseudo-fixed bed reactor using strong acidic ionic liquid under suitable reaction conditions.

In short, the strong acidic ionic liquid of the present invention is mainly formulated with a quaternary ammonium halide ($[R'NR_3]^+X^-$) or a quaternary phosphonium halide ($[R'PR_3]^+X^-$) and aluminum trichloride ($AlCl_3$). Quaternary ammonium cations and quaternary phosphonium cations include tetraalkylammonium, dialkylpyridinium, dialkylimidazolium, and tetraalkylphosphonium. Halide ions include, for example, fluoride, chloride, bromide, and iodide. In the ionic liquid, a mole fraction of aluminum trichloride is about 0.5-0.9. After floating from bottom to top of the reactor as a droplet, the reactants flow out from a side tube. A feeding rate is 0.1-10 g/min, and a temperature for the isomerization is between 25-120° C.

Therefore, cycloalkane isomerization can be effectively performed in a pseudo-fixed bed reactor by using a suitable reaction column length and packing under suitable reaction conditions. This reaction manner is similar to that in a fixed bed reactor, and can be used in cycloalkane isomerization with high reaction activity, for example, in isomerization of endo-THDCPD into exo-THDCPD (i.e. JP-10), and isomerization of exo-THDCPD into adamantane, which is a simple and effective catalytic process.

Such a process is used under conditions that (1) reactants and products are immiscible with ionic liquid, (2) density of the reactants and products is less than the ionic liquid, and (3) reaction has sufficient reaction activity.

Though the present invention has been described above with reference to preferred embodiments, however, the present invention is not limited to these embodiments, and equivalent alternatives of changes and modifications made by any person of skill in the art without departing spirit and scope of the present invention are still in patent protection scope of the present invention.

What is claimed is:

1. A method for synthesizing exo-tetrahydrodicyclopentadiene (exo-THDCPD) using a pseudo-fixed bed ionic liquid reactor, comprising isomerizing an endo-tetrahydrodicyclopentadiene (endo-THDCPD) as a reaction feed with an acidic ionic liquid of aluminum trichloride in a pseudo-fixed bed ionic liquid reactor, wherein reactants float as a droplet from bottom to top of the pseudo-fixed bed reactor, and finally are discharged from a side tube, and wherein a mole fraction of aluminum trichloride in the acidic ionic liquid of aluminum trichloride is from 0.5 to 0.9, a feeding rate of the reaction feed is 0.1-10 g/min, and a temperature for the isomerization is between 25-120° C.

2. The method for synthesizing exo-THDCPD using a pseudo-fixed bed ionic liquid reactor according to claim 1, wherein the reaction feed further comprises a hydrocarbon, and a content of the endo-THDCPD in the reaction feed is 10-100 vol %.

3. The method for synthesizing exo-THDCPD using a pseudo-fixed bed ionic liquid reactor according to claim 1, wherein the acidic ionic liquid of aluminum trichloride is a strong acidic ionic liquid of aluminum trichloride.

4. The method for synthesizing exo-THDCPD using a pseudo-fixed bed ionic liquid reactor according to claim 1, wherein the acidic ionic liquid of aluminum trichloride is formulated with a quaternary ammonium halide ($[R'NR_3]^+X^-$) or a quaternary phosphonium halide ($[R'PR_3]^+X^-$) and aluminum trichloride ($AlCl_3$).

5. The method for synthesizing exo-THDCPD using a pseudo-fixed bed ionic liquid reactor according to claim 1, wherein the mole fraction of aluminum trichloride in the acidic ionic liquid of aluminum trichloride is preferably from 0.55 to 0.70.

6. The method for synthesizing exo-THDCPD using a pseudo-fixed bed ionic liquid reactor according to claim 1, wherein the temperature for the isomerization is preferably between 50-80° C.

7. The method for synthesizing exo-THDCPD using a pseudo-fixed bed ionic liquid reactor according to claim 1, wherein the feeding rate of the reaction feed is preferably 0.5-2.0 g/min.

8. The method for synthesizing exo-THDCPD using a pseudo-fixed bed ionic liquid reactor according to claim 1, wherein the ionic liquid reactor is equipped with a baffle or filled with packing.

9. The method for synthesizing exo-THDCPD using a pseudo-fixed bed ionic liquid reactor according to claim 1, wherein the packing of the pseudo-fixed bed reactor is a glass bead, a ceramic particle, or an acid tolerant material.

10. The method for synthesizing exo-THDCPD using a pseudo-fixed bed ionic liquid reactor according to claim 1, wherein the pseudo-fixed bed reactor is a vertical pseudo-fixed bed reactor or a spiral pseudo-fixed bed reactor.

* * * * *